(12) United States Patent
Philips

(10) Patent No.: US 6,290,717 B1
(45) Date of Patent: Sep. 18, 2001

(54) TEMPERATURE PROBE AND INTERCONNECT CABLE FOR HYPOTHERMIA CATHETER TEMPERATURE FEEDBACK

(75) Inventor: Peter J. Philips, Trabuco Canyon, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/282,971

(22) Filed: Mar. 31, 1999

(51) Int. Cl.[7] .................................................. A61F 7/12
(52) U.S. Cl. ............................................. 607/113; 600/20
(58) Field of Search .................... 607/96, 99, 102, 607/104, 105, 113; 606/32, 34, 41; 600/20, 21

(56) References Cited

U.S. PATENT DOCUMENTS

| | | | | |
|---|---|---|---|---|
| 4,415,219 | * | 11/1983 | Kuhl et al. | 439/694 |
| 5,269,311 | * | 12/1993 | Kirchner et al. | 600/485 |
| 5,357,954 | * | 10/1994 | Shigezawa et al. | 128/634 |
| 5,628,771 | * | 5/1997 | Mizukawa et al. | 607/102 |
| 5,871,481 | * | 2/1999 | Kannenberg et al. | 606/34 |

* cited by examiner

*Primary Examiner*—Linda C. M. Dvorak
*Assistant Examiner*—R. Kearney
(74) *Attorney, Agent, or Firm*—John L. Rogitz

(57) ABSTRACT

A disposable esophageal probe having dual temperature elements is connected to a cooling catheter controller via a reusable interconnect line to provide redundancy in temperature feedback to the controller, namely, to provide both a control temperature feedback signal and an alarm temperature feedback signal to the controller.

19 Claims, 2 Drawing Sheets

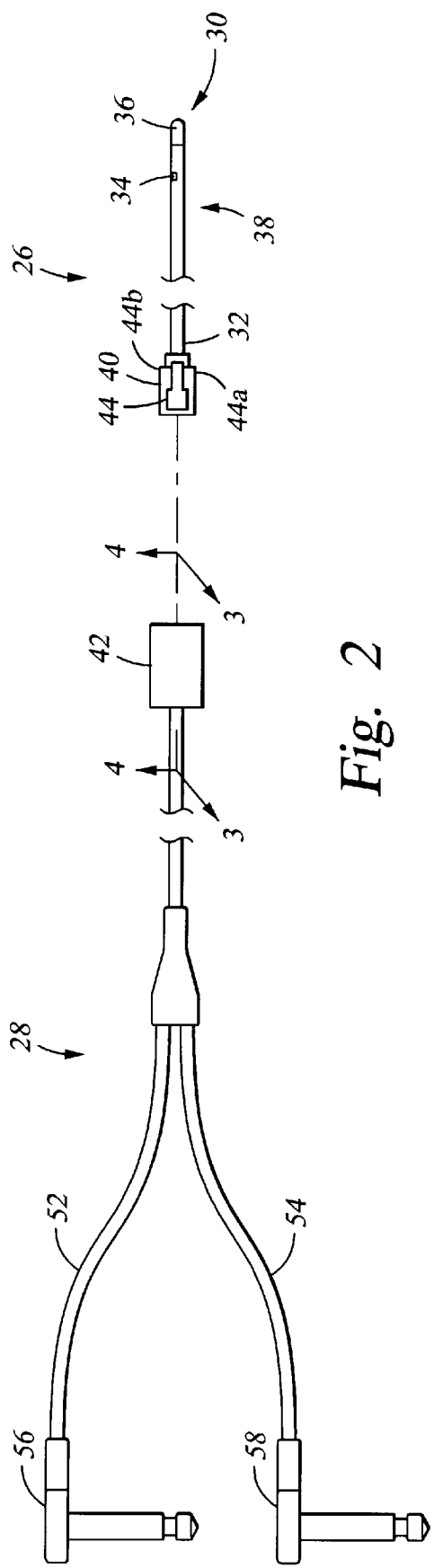
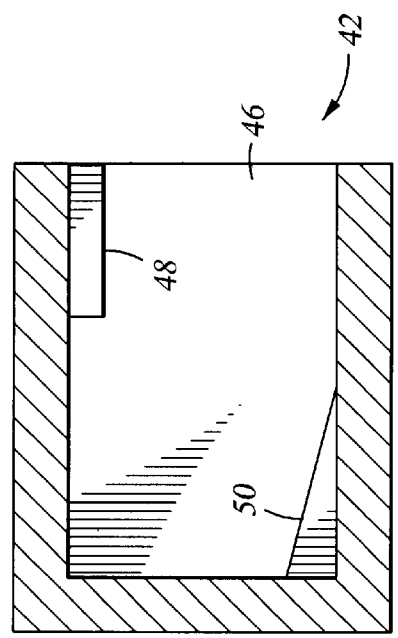
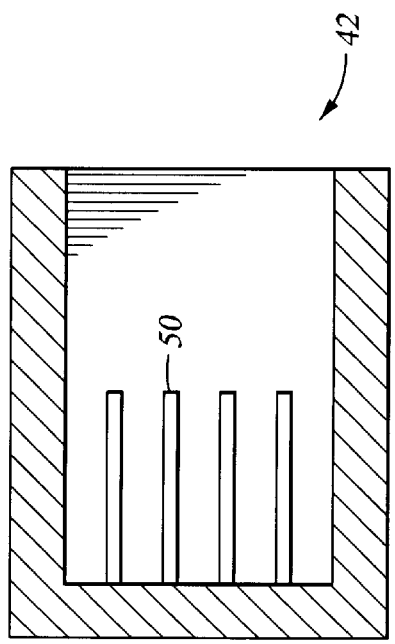

TEMPERATURE PROBE AND INTERCONNECT CABLE FOR HYPOTHERMIA CATHETER TEMPERATURE FEEDBACK

FIELD OF THE INVENTION

The present invention relates generally to methods and apparatus for cooling patients for therapeutic purposes, and more particularly to systems for measuring temperature in a patient to provide a feedback control signal for controlling a cooling catheter.

BACKGROUND

It has been discovered that the medical outcome for a patient suffering from severe brain trauma or from ischemia caused by stroke or heart attack is degraded if the patient's body temperature rises above normal (38° C.). It is further believed that the medical outcome for many such patients might be significantly improved if the patients were to be cooled relatively quickly to around 32° C. for a short period, e.g., 24–72 hours. Apart from the therapeutic benefits of hypothermia, the outcomes for brain trauma or ischemia patients that develop fevers is worse than for patients that do not develop fevers. Consequently, temperature management for such patients is important, even when hypothermia is not to be used to treat the patients.

The affected organ, in any case, is the brain. Accordingly, systems and methods have been disclosed that propose cooling blood flowing to the brain through the carotid artery. An example of such systems and methods is disclosed in co-pending U.S. patent application Ser. No. 09/063,984, filed Apr. 21, 1998, owned by the present assignee and incorporated herein by reference. In the referenced application, various catheters are disclosed which can be advanced into a patient's carotid artery and through which coolant can be pumped in a closed circuit, to remove heat from the blood in the carotid artery and thereby cool the brain. The referenced devices have the advantage over other methods of cooling (e.g., wrapping patients in cold blankets) of being controllable, relatively easy to use, and of being capable of rapidly cooling and maintaining blood temperature at a desired set point.

As recognized in co-pending U.S. patent application Ser. No. 09/133,813, filed Aug. 13, 1998, owned by the present assignee and incorporated herein by reference, the above-mentioned advantages in treating brain trauma/ischemic patients by cooling can also be realized by cooling the patient's entire body, i.e., by inducing systemic hypothermia. The advantage of systemic hypothermia is that, as recognized by the present assignee, to induce systemic hypothermia a cooling catheter or other cooling device need not be advanced into the blood supply of the brain, but rather can be easily and quickly placed into the relatively large vena cava of the central venous system.

Moreover, since many patients already are intubated with central venous catheters for other clinically approved purposes anyway, providing a central venous catheter that can also cool the blood, if only to manage temperature and thereby ameliorate fever spikes, requires no additional surgical procedures for those patients. A cooling central venous catheter is disclosed in the present assignee's co-pending U.S. patent application Ser. No. 09/253,109, filed Feb. 19, 1999 and incorporated herein by reference.

To supply coolant such as saline to the above-disclosed catheters, a cooling system such as the present assignee's system disclosed in co-pending U.S. patent application Ser. No. 09/220,897, filed Dec. 24, 1998 and incorporated herein by reference, can be used to remove heat from the coolant and return the coolant to the catheter in a closed loop heat exchange system. An alternate system is the thermoelectric cooler (TEC)-based system owned by the present assignee and disclosed in co-pending U.S. patent application Ser. No. 09/260,950, filed Mar. 2, 1999, also incorporated herein by reference. In any case, a cooling system controller preferably maintains temperature at a desired setpoint, be it normothermic or hypothermic. As recognized herein, to facilitate such temperature maintenance, it is necessary to measure patient temperature.

As understood by the present invention, esophageal temperature is a preferred parameter to use because it is more sensitive to body core temperature changes than, e.g., rectal temperature. As also understood by the present invention, for ease of use and to avoid burdensome sterilization procedures, the portion of an esophageal temperature sensor that is advanced into a patient should be disposable. Portions not in contact with the patient, however, need not be disposable. The present invention is provided with these considerations in mind.

SUMMARY OF THE INVENTION

A temperature probe for a therapeutic cooling catheter system includes an elongated probe body that has a distal end and a proximal end, and that is configured for being advanced into a patient with the distal end located in the patient's body and the proximal end located outside the patient's body. First and second temperature sensors, preferably thermistors, are located at or near the distal end of the probe body for generating respective first and second temperature signals. Also, a probe connector is located at or near the proximal end of the probe body, and a reusable interconnect cable has a cable connector configured for engaging the probe connector and at least one controller connector electrically connected to the cable connector and engageable with a controller.

In a preferred embodiment, the probe body is configured for advancement into a patient's esophagus. Also in the preferred embodiment, the probe connector snappingly engages the cable connector. One of the connectors preferably is a male telephone connector and the other connector is a female telephone connector. More specifically, the preferred probe connector includes an outwardly biased pivot arm and the cable connector includes a socket including at least one retainer rail, and the arm snappingly engages the rail when the probe connector is advanced into the cable connector. The arm of the probe connector extends beyond the cable connector when the probe connector is fully engaged with the cable connector, with the arm being manipulable to cause the arm to clear the rail and thereby permit disengagement of the probe connector from the cable connector.

As disclosed in greater detail below, the cable includes first and second controller segments terminating in respective first and second controller connectors. Each controller connector is engageable with the controller. The controller connectors can be phone plugs.

With further regard to the controller, the first temperature sensor generates a control feedback signal that is useful by the controller for controlling a heat exchanger. Also, the second temperature sensor generates an alarm feedback signal useful by the controller for generating an alarm signal. The system is disclosed in combination with a heat exchange catheter in closed loop fluid communication with the heat exchanger.

In another aspect, a controller includes a program of instructions for undertaking method acts for controlling a heat exchanger. These acts includes receiving, from first and second temperature sensors, respective first and second patient esophageal temperature signals. Also, the method acts includes controlling a heat exchanger for a cooling catheter in response to at least the first signal, and generating an alarm signal when the second signal reaches a predetermined setpoint.

In still another aspect, an esophageal temperature sensing apparatus includes first and second temperature sensors supported by a disposable probe body. The probe body is configured for advancing the sensors into a patient's esophagus, with the proximal end of the probe body remaining outside the patient's body at all times. A male or female telephone probe connector is at the proximal end, and an interconnect cable having a female or male telephone cable connector is selectively snappingly engageable with the probe connector. Moreover, a controller connector is engageable with a controller of a closed circuit cooling catheter heat exchange system. As set forth below, the interconnect cable establishes electrical connectivity between the cable connector and the controller connector.

The details of the present invention, both as to its structure and operation, can best be understood in reference to the accompanying drawings, in which like reference numerals refer to like parts, and in which:

BRIEF DESCRIPTION OF THE DRAWINGS

FIG. 2 is a top view of the probe body in an exploded relationship with the interconnect cable;

FIG. 3 is a cross-sectional view of the cable connector as seen along the line 3—3 in FIG. 2;

FIG. 4 is a cross-sectional view of the cable connector as seen along the line 4—4 in FIG. 2.

DETAILED DESCRIPTION OF THE PREFERRED EMBODIMENT

Figure 1:
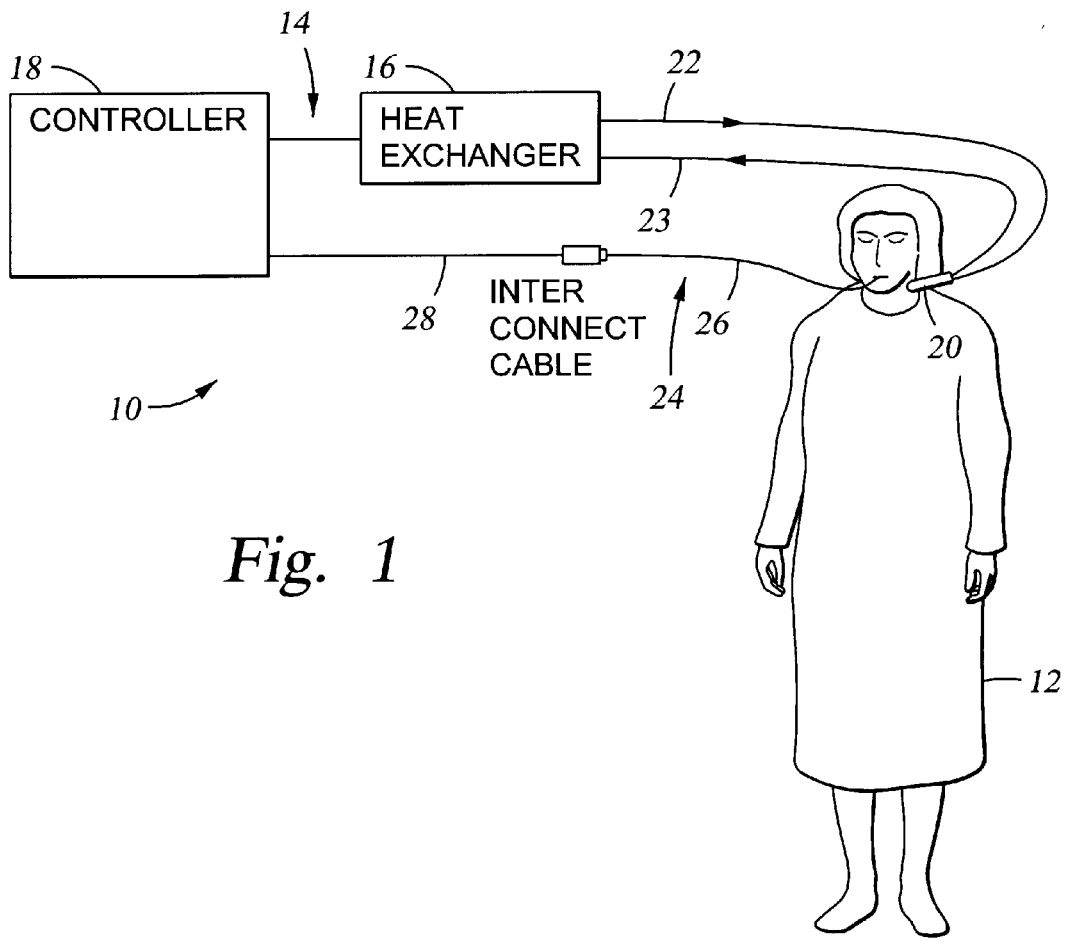
FIG. 1 is a schematic view of the present invention in its intended environment.

Referring initially to FIG. 1, a therapeutic system, generally designated 10, is shown for establishing and maintaining hypothermia in a patient 12, or for attenuating a fever spike in a patient and then maintaining normal body temperature in the patient. As shown, the system 10 includes a cooling system 14 that can be a water-bath system or a TEC-based system such as either of the systems disclosed in the last two of the above-referenced applications. In any case, the cooling system 14 can be considered a source of coolant, preferably sterile saline, for the catheters of the present invention.

As set forth in the last two of the above-referenced applications, the cooling system 14 can include a heat exchange system 16 including a pump. The pump and/or heat exchange elements in the heat exchange system 16 are controlled by a controller 18. The controller 18 can be implemented by a software-executing processor or by discrete logic circuits or other electronic circuitry device to establish a desired patient temperature by appropriately controlling the pump and/or heat exchanger in response to a temperature signal derived from one or more sensors in the patient 12.

As shown in FIG. 1, a catheter 20 can communicate with the cooling system 14 via coolant supply and return lines 22, 23. The coolant lines 22, 23 can be IV lines or tubes or other suitable fluid conduits, such as metal (steel) tubes. When the coolant lines 22, 23 are plastic tubes, they can be connected to the catheter 20 and the cooling system 14 by suitable connecting structure, such as Luer fittings, interference fits, solvent bonding, heat staking, ultrasonic welding, and the like. The catheter 20 can be any of the catheters disclosed in the first two of the above-referenced applications in which coolant is circulated in a closed fluid communication loop to remove heat from the patient 12. The catheter 20 is advanced (preferably through an introducer sheath) into the patient 12 through a neck entry point or femoral entry point to establish hypothermia in the patient 12, or to attenuate a fever back to normal body temperature. Preferably, the catheter 20 is advanced into the central venous system, and more preferably into the vena cava, either through the subclavian vein or jugular vein or femoral vein.

To enable the controller 18 to control the heat exchanger 16, patient temperature feedback is required. As understood by the present invention, patient safety standards can dictate that the feedback be redundant, such that if one temperature sensor fails, the second sensor can still monitor temperature. As further understood by the present invention, while two sensors are desirable, it is also desirable to minimize the number of probes that are advanced into a patient.

Accordingly, a temperature feedback apparatus 24 including a probe body 26 and an interconnect cable 28 is provided herein to interconnect at least first and second temperature sensors (not shown in FIG. 1) that are positioned in the patient 12 to the controller 18. Although the sensors can be positioned in, e.g., the rectum, bladder, or near the tympanic membrane of the patient 12, they are preferably positioned in the esophagus.

FIGS. 2–4 show the details of the temperature feedback apparatus 24. As can be appreciated in reference to FIG. 2, the probe body 26 is a disposable elongated probe body having a distal end 30 and a proximal end 32. In the preferred embodiment, the probe body 26 is configured for advancing the probe body into a patient's esophagus with the distal end 30 located in the patient's body and the proximal end 32 located outside the patient's body.

At least first and second temperature sensors 34, 36 are located at or near the distal end 30 of the probe body 26. The sensors are preferably YSI400 series thermistors that generate respective first and second temperature signals. Each thermistor is electrically connected to two electrical leads in accordance with means known in the art, and the leads extend through the probe body 26 to the proximal end 32 of the body 26. Surrounding the leads and the sensors 34, 36 is a plastic biocompatible sheath 38 that can be coated with antimicrobial coatings and/or antithrombogenic coatings. Also, the sensors 34, 36 are isolated from each other by placing the first sensor 34 inside a first insulative sheath and then placing the first sheath and second sensor 36 inside a second sheath. Sensors other than thermistors, such as thermocouples, resistance temperature detectors (RTDs), and the like can be used.

A probe connector 40 is located at or near the proximal end 32 of the probe body 26. The interconnect cable 28, which preferably is reusable, has a cable connector 42 that is configured for easily and quickly engaging and disengaging the probe connector 40, preferably in a snapping or interference fit. In one preferred embodiment, the probe connector 40 is a male telephone connector and cable connector is a female telephone connector, although these structures can be reversed.

Accordingly, in the preferred embodiment shown in FIGS. 2–4, the probe connector 40 includes an outwardly biased pivot arm 44 that is formed with transverse ears 44a and a narrow extension 44b. The cable connector 42, on the other hand, includes a socket 46 that in turn includes at least one retainer rail 48. The arm 44 of the probe connector 40 rides against the rail 48 when the probe connector 40 is advanced into the cable connector 42 to overcome the outward bias of the arm 44. When the probe connector 40 has been advanced a sufficient distance into the cable connector 42, the ears 44a clear the rail 48, causing the pivot arm 44 to snap outwardly under the influence of its material bias, thereby engaging the connectors 40, 42. Electrical contact between the connectors 40, 42 is established between a connector ramp 50 in the cable connector 42 and complimentarily-formed structure (not shown) on the probe connector 40.

When the connectors 40, 42 are fully engaged, the extension 44b of the probe connector 40 extends beyond the cable connector 42. The extension 44b can be manipulated to cause the arm 44 to clear the rail 48 and thereby permit the connectors 40, 42 to be disengaged by pulling the probe connector 40 out of the cable connector 42.

In the embodiment shown in FIG. 2, the cable 28 includes first and second controller segments 52, 54 that terminate in respective first and second controller connectors 56, 58. It is to be understood that the first controller connector 56 is electrically connected to the first sensor 34 via the first segment 52 and probe body 26 when the connectors 40, 42 are engaged, and the second controller connector 58 is electrically connected to the second sensor 36 via the second segment 54 and probe body 26 under these circumstances. In accordance with the present invention, each controller connector 56, 58 is engageable with the controller 18 (FIG. 1) to thereby establish an electrical path between the sensors 34, 36 and the controller 18. Preferably, the controller connectors 56, 58 are phone plugs.

Per the present invention the first temperature sensor 34 generates a control feedback signal that is useful by the controller 18 for controlling the heat exchanger 16. Also, the second temperature sensor 36 generates an alarm feedback signal that is useful by the controller 18 for generating an alarm signal.

Figure 5:
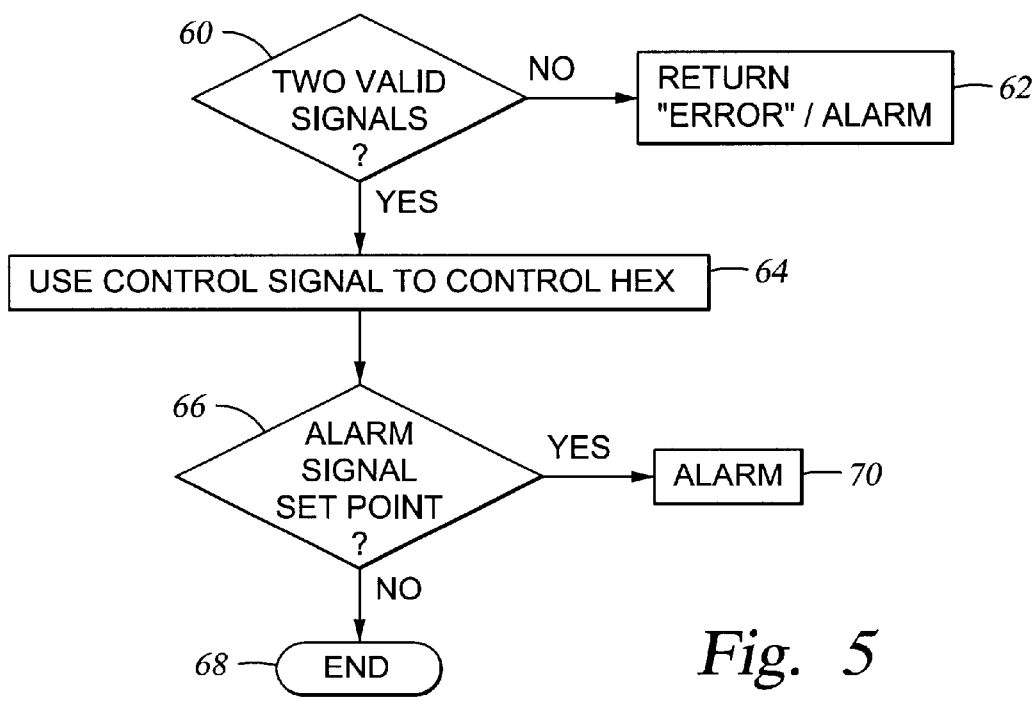
FIG. 5 is a flow chart of the logic of the present invention.

FIG. 5 shows the logic of the present controller 18 in treating the signals from the sensors 34, 36. Commencing at decision diamond 60, it is determined whether two valid signals have been received. If not, indicating an undesirable loss of redundancy, the process moves to block 62 to return an error signal or alarm. Otherwise, the logic moves to block 64.

At block 64, the controller 18 uses the control signal from the first sensor 34 to control the heat exchanger 16 as set forth in the latter two of the above-disclosed patent applications. Proceeding to decision diamond 66, it is determined whether the second signal, i.e., the signal from the second sensor 36, has reached a high temperature or low temperature setpoint. If not, the process ends at state 68, but if a setpoint has been reached an alarm is generated at block 70. The process, although shown in flow chart format for ease of disclosure, can be a continuous state process.

While the particular TEMPERATURE PROBE AND INTERCONNECT CABLE FOR HYPOTHERMIA CATHETER TEMPERATURE FEEDBACK as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. ?112, sixth paragraph, unless the element is expressly recited using the phrase "means for".

What is claimed is:

1. A temperature probe, comprising:
   an elongated probe body having a distal end and a proximal end, the probe body being configured for advancing the probe body into a patient with the distal end located in the patient's body and the proximal end located outside the patient's body;
   at least first and second temperature sensors located at or near the distal end of the probe body generating respective first and second temperature signals;
   a probe connector located at or near the proximal end of the probe body; and
   a reusable interconnect cable having a cable connector configured for engaging the probe connector and at least one controller connector electrically connected to the cable connector and engageable with a controller, wherein one of: the probe connector, and the cable connector, is a male telephone connector and the other of: the probe connector, and the cable connector, is a female telephone connector.

2. The probe of claim 1, wherein the probe body is configured for advancement into a patient's esophagus.

3. The probe of claim 1, wherein the probe connector snappingly engages the cable connector.

4. The probe of claim 3, wherein the probe connector includes an outwardly biased pivot arm and the cable connector includes a socket including at least one retainer rail, and the arm snappingly engages the rail when the probe connector is advanced into the cable connector.

5. The probe of claim 4, wherein at least a portion of the arm of the probe connector extends beyond the cable connector when the probe connector is fully engaged with the cable connector, the portion being manipulable to cause the arm to clear the rail and thereby permit disengagement of the probe connector from the cable connector.

6. The probe of claim 1, wherein the sensors are thermistors and the probe body is disposable.

7. The probe of claim 1, wherein the cable includes first and second controller segments terminating in respective first and second controller connectors, each controller connector being engageable with the controller.

8. The probe of claim 7, wherein the controller connectors are phone plugs.

9. The probe of claim 1, in combination with the controller, wherein the first temperature sensor generates a control feedback signal useful by the controller for controlling a heat exchanger, and wherein the second temperature sensor generates an alarm feedback signal useful by the controller for generating an alarm signal.

10. The combination of claim 9, in further combination with the heat exchanger.

11. The combination of claim 10, in further combination with a heat exchange catheter in closed loop fluid communication with the heat exchanger.

12. A controller including a program of instructions undertaking method acts for controlling a heat exchanger, the method acts comprising:

receiving, from first and second temperature sensors, respective first and second patient esophageal temperature signals;

providing a cooling catheter in which coolant is circulated in a closed fluid communication loop;

controlling a heat exchanger for the cooling catheter in response to at least the first signal; and generating an alarm signal when the second signal reaches a predetermined setpoint.

13. The controller of claim 12, wherein the method acts further comprise generating an alarm signal when the second signal indicates a failure of the second sensor.

14. A temperature sensing apparatus, comprising:

at least first and second temperature sensors supported by a disposable probe body configured for advancing the sensors into a patient, the probe body defining a proximal end remaining outside the patient's body at all times;

a male or female telephone probe connector at the proximal end;

an interconnect cable having a female or male telephone cable connector selectively snappingly engageable with the probe connector;

at least one controller connector engageable with a controller of a closed circuit cooling catheter heat exchange system, the interconnect cable establishing electrical connectivity between the cable connector and the controller connector.

15. The apparatus of claim 14, comprising two controller connectors.

16. The apparatus of claim 14, in combination with the controller.

17. The combination of claim 16, wherein the controller includes a program of instructions undertaking method acts for controlling a heat exchanger, the method acts comprising:

receiving, from the first and second temperature sensors, respective first and second patient esophageal temperature signals;

controlling the heat exchanger in response to at least the first signal; and generating an alarm signal when the second signal reaches a predetermined setpoint.

18. The combination of claim 17, wherein the method acts further comprise generating an alarm signal when the second signal indicates a failure of the second sensor.

19. The combination of claim 18, in further combination with combination with a heat exchange catheter in closed loop fluid communication with the heat exchanger.

* * * * *